United States Patent
Chen et al.

(10) Patent No.: US 11,744,921 B2
(45) Date of Patent: Sep. 5, 2023

(54) SURGICAL IMPLANT MATERIAL FOR ASSISTED REPAIR OF MUSCLE MECHANICS AND METHOD OF PREPARING THE SAME

(71) Applicants: Lai Chen, Shenzhen (CN); PKU-HKUST ShenZhen-HongKong Institution, Shenzhen (CN)

(72) Inventors: Lai Chen, Shenzhen (CN); Xi Ting Fei, Shenzhen (CN); Sheng Li Yuan, Shenzhen (CN)

(73) Assignees: Lai Chen, Shenzhen (CN); PKU-HKUST SHENZHEN-HONGKONG INSTITUTION, Shenzhen (CN)

( * ) Notice: Subject to any disclaimer, the term of this patent is extended or adjusted under 35 U.S.C. 154(b) by 643 days.

(21) Appl. No.: 16/749,802

(22) Filed: Jan. 22, 2020

(65) Prior Publication Data
US 2021/0128787 A1 May 6, 2021

(30) Foreign Application Priority Data
Nov. 4, 2019 (CN) .......................... 201911063845.4

(51) Int. Cl.
*A61L 27/20* (2006.01)
*A61L 27/24* (2006.01)
*A61L 27/48* (2006.01)
*A61F 2/00* (2006.01)
*A61L 27/36* (2006.01)

(52) U.S. Cl.
CPC ............ *A61L 27/48* (2013.01); *A61F 2/0063* (2013.01); *A61L 27/20* (2013.01); *A61L 27/24* (2013.01); *A61L 27/3637* (2013.01); *A61L 27/3687* (2013.01); *A61F 2002/0081* (2013.01); *A61F 2240/001* (2013.01)

(58) Field of Classification Search
CPC .. A61F 2/0063; A61F 2240/001; A61L 27/24; A61L 2430/30; A61L 2420/02; A61L 27/20
See application file for complete search history.

(56) References Cited

FOREIGN PATENT DOCUMENTS

| CN | 102526795 A | * | 7/2012 | ............ A61L 15/28 |
|----|---|---|---|---|
| CN | 102352051 B | * | 9/2013 | ............ A61L 27/54 |
| CN | 103861146 A |   | 6/2014 | |
| CN | 107115563 A |   | 9/2017 | |
| CN | 108079386 A |   | 5/2018 | |
| CN | 108329507 A |   | 7/2018 | |

OTHER PUBLICATIONS

Ul-Islam et al. Bacterial cellulose composites: Synthetic strategies and multiple applications in bio-medical and electro-conductive fields. Biotechnol. J. 2015;10:1847-1861.*
Portela et al. Bacterial cellulose: a versatile biopolymer for wound dressing applications. Microb Biotechnol. 2019;12(4):586-610.*
Lee et al. The effect of bacterial cellulose membrane compared with collagen membrane on guided bone regeneration. J Adv Prosthodont. 2015;7:484-95.*

* cited by examiner

*Primary Examiner* — Lynn Y Fan
(74) *Attorney, Agent, or Firm* — MUNCY, GEISSLER, OLDS & LOWE, P.C.

(57) ABSTRACT

The present invention provides a surgical implant material for assisted repair of muscle mechanics and a method of preparing the same. The surgical implant material for assisted repair of muscle mechanics comprises a collagen compound within a net-like bacterial cellulose base material. A bacterial cellulose base material is placed into solution of collagen, treated via vortex shaking, dried at room temperature; and then immersed in an aqueous solution of an aldehyde compound under vacuum to react for 10 to 30 minutes, thereby producing the surgical implant material for assisted repair of muscle mechanics. The surgical implant material of the present invention can effectively improve the biocompability, and maintain the flexibility, smoothness and fitness of the base material to reduce the damage to surrounding tissues, thereby reducing the bleeding and inflammatory response. Meanwhile, the processing conditions of the preparation method is more reasonable and convenient to control, and more suitable for industrial scale-up.

2 Claims, No Drawings

SURGICAL IMPLANT MATERIAL FOR ASSISTED REPAIR OF MUSCLE MECHANICS AND METHOD OF PREPARING THE SAME

FIELD OF THE INVENTION

The present invention relates to a surgical material for medicine and a method of preparing the same, especially to a surgical implant material for assisted repair of muscle mechanics and a method of preparing the same.

BACKGROUND OF THE INVENTION

Pelvic support comes from conjunctive tissues of pelvic floor muscles (fascias), as well as thickened parts of ligament. However, the pelvic floor muscles of women will gradually relax with increasing age. Once the fascias and ligaments cannot bear the corresponding weight, the pelvic organs will drop and enter vaginal walls, thereby causing pelvic floor dysfunctions, such as, urinary incontinence, uterine prolapse, etc., of which the incidence rate is up to around 40% to 60% in middle-aged and elderly women. Surgical implantation of the corresponding material is the unique effective treatment. Currently, all such surgical implant materials as used in clinical practice are mainly imported from Europe and the U.S. States, e.g., from Johnson & Johnson, C. R. Bard, PFM Medical, Inc. and the like. And these surgical implant material used in clinical practice are all made by woven polypropylene, while the improved type is made by coating the polypropylene mesh with collagen or metal. However, it is worth to note that FDA issued a warning on the use of mesh in pelvic floor organ prolapse and urinary incontinence surgery in July, 2011, and banned the sale of all the currently approved transvaginal surgical implant materials (also known as meshes or patches) on Apr. 16, 2019. This shows that the defects of the polypropylene materials for surgical implantation have significantly affected the sale and clinical use of such materials.

To address the defects of polypropylene materials for surgical implantation, recently it is also proposed to utilize bacterial celluloses to produce mesh sheets for use as gynecological pelvic floor patches, as disclosed in the Chinese Patent Application No. 201410089918.8. However, when the mesh sheet is used for implantation into the body (e.g., into the vagina), it is likely to fold and bend with movement due to its thinness and softness, resulting that the surrounding tissues cannot grow into the mesh, thereby causing severe inflammatory response, and thus the failure of operation. In addition, when the bacterial celluloses are used in gynecological pelvic floor patches, the recovery period after surgery is too long because the bacterial celluloses have poor compatibility with pelvic floor tissues and thus the tissues grows slowly. Thus, the Chinese Patent Application Nos. 201710283604.5 and 201810179642.0 propose methods of improving the bacterial celluloses for use in patches. Nevertheless, it is founded in practice that the materials have still disadvantages, such as poor compatibility with tissues. The foregoing information is detailed examples of assisted repair against the cause of muscle mechanic relaxation in the field of gynecological pelvic diseases. Auxiliary repair materials are also required when tissue damage to muscle mechanics occurs in other internal tissue muscles (e.g., those in esophagus, chest, and the like).

SUMMARY OF THE INVENTION

The present invention provides a surgical implant material for assisted repair of muscle mechanics which can effectively reduce the friction with surrounding tissues and have good tissue compatibility, and a method of preparing the same. The present invention is achieved by the following technical solutions.

A surgical implant material for assisted repair of muscle mechanics comprises a collagen compound in a net-like bacterial cellulose base material, in which the percent of nitrogen atoms is around 5-15%. The bacterial celluloses prepared in accordance with the method as disclosed in the Chinese Patent Application No. 201710283604.5 can be used as base material, but the impurities (such as, endotoxin or the like) contained the base material itself should meet the national standards for surgical implant materials. For instance, the used bacterial cellulose base material can be treated by the method in accordance with the Chinese Patent Application No. 201810180455.4 for removal of endotoxin so as to allow the material to meet the national standards.

It is empirically found that a material exhibits more superior performances when it has a root-mean-square (RMS) surface roughness of 40-50 nm.

A method of preparing the aforesaid surgical implant material for assisted repair of muscle mechanics comprises that a net-like bacterial cellulose base material is placed into a solution of collagen at a certain concentration, treated in a manner of vortex shaking for 30 seconds to 10 minutes, dried at room temperature; next the base material is placed into an aqueous solution of an aldehyde compound at a concentration of 0.5-10 wt % at 30-50° C. for immersion for 50-70 minutes; and then the material treated by immersion undergo a reaction in a vacuum environment having a vacuum degree of 0.06-0.5 Mpa at 60-120° C. for 10-30 min, thereby producing the surgical implant material for assisted repair of muscle mechanics. The net-like bacterial cellulose base material can utilize the bacterial cellulose mesh sheets prepared in accordance with the method of the Chinese Patent Application No. 201710283604.5 as base material, but the impurities (such as, endotoxin or the like) of the base material should meet the national standards for surgical implant materials. For instance, the used bacterial cellulose base material can be treated by the method in accordance with the Chinese Patent Application No. 201810180455.4 for removal of endotoxin so as to allow the material to meet the national standards.

Massive experiments show that when glutaraldehyde is used as the aldehyde compound, the best result is achieved. When the base material is placed into the aqueous solution of the aldehyde compound at 30-50° C. for immersion, the best result is achieved by disturbing the aqueous solution. The disturbing can be performed by a method available from the currently technologies, such as, shaking in a shaker, magnetic stirring, etc.

The aqueous solution of the aldehyde compound can further comprise a water-soluble inorganic aluminum salt, and the preferable concentration of the inorganic aluminum salt in the aqueous solution is 0.1-3%.

In comparison with the current technologies, the present invention has the following advantages:

1. The surgical implant material for assisted repair of muscle mechanics prepared in accordance with the present invention have crosslinked collagen in both the surface and gap between fibers of the bacterial cellulose material. Thus, on one hand, the materials have properties like softness, smoothness, fitness of the bacterial cellulose base so as to reduce the damage to surrounding tissues caused by friction, thereby reducing the bleeding and inflammatory responses; and on the other hand, the crosslinked collagen compound allow the materials to have good biocompatibility and thus good fusion with tissues of posterior vaginal walls.

2. The method of the present invention specially selects attaching the collagen compound to the base material by means of vortex shaking upon placing the net-like bacterial cellulose base material in to the solution of the collagen compound at a certain concentration. For example, a vortex-genie 2 type vortex shaker can be used, e.g., adjusted to an appropriate gear, such as, Gear 8-9, so that the maximum adhesion can be achieved within 10 minutes. Such method saves both time and labor. It not only overcomes the time-consuming shortcoming of the existing standing method (typically, more than 24 hours) for preparing such surgical implant materials, but also addresses the material-wasting disadvantage of spraying method.

3. In the method of the present invention, it is first found that the reaction between the aldehyde and the hydroxyl groups can be completed at a temperature of 100° C. or below with 10-30 min when the base material which is immersed with the aqueous solution of the aldehyde compound and to which a collagen compound is attached is placed within a vacuum environment. In the contrast, in the current technology, the reaction between the aldehyde and the hydroxyl groups is performed at an elevated temperature and an ambient pressure but within a time period of 10-20 seconds. Such reaction conditions are inconvenient to control, and likely to overreact to cause embrittlement of surgical implant materials. Thus, the method of the present invention has convenient-to-control reaction conditions and relatively high material yield, and thus facilitate to industrial scale-up.

DETAILED DESCRIPTION OF THE INVENTION

Embodiment 1

A method of preparing the aforesaid surgical implant material for assisted repair of muscle mechanics was carried out by the steps of:

Step 1: dissolving collagen into acetic acid to give a 3 wt % solution of collagen in acetic acid;

Step 2; placing a net-like bacterial cellulose base material which was purified by removal of endotoxin in accordance with CN201810180455.4 into the solution in acetic acid prepared in Step 1, treating the mixture by means of vortex shaking with a vortex-genie 2 type vortex shaker adjusted to Gear 8 for 10 minutes, and hanging to dry at room temperature;

Step 3: placing the base material obtained in Step 2 into a 3 wt % aqueous solution of glutaraldehyde, adding 0.02% $Al_2(SO4)_3$ into the solution, and immersing at 37° C. in a shaker at 110 rpm for 60 minutes; and Step 4: Reacting the material immersed in Step 3 at 90° C. in a vacuum drying oven at a vacuum degree of 0.08 Mpa for 30 min, to produce the surgical implant material for assisted repair of muscle mechanics.

Embodiment 2

The material of Example 1, a bacterial cellulose base material (Comparative Example 1) and a bacterial cellulose surgical implant material coated with collagen on the surface and prepared in accordance with the prior art (Comparative Example 2) were detected for the content of nitrogen atoms and the surface roughness of materials, respectively. The results are shown in Table 1.

TABLE 1

| Sample | Percent of Nitrogen Atoms | RMS Surface Roughness, nm |
| --- | --- | --- |
| Comparative Example 1 | 0 | 27.5 |
| Comparative Example 2 | 1.7 | 75.6 |
| Example 1 | 5.56 | 45.7 |

The aforesaid measurements show that as compared with the material of Comparative Example 2, the material of Example 1 enables the bacterial cellulose to comprise more biocompatibility-improving collagen (the percent of nitrogen element reflects the content of collagen because nitrogen is contained only in collagen). Meanwhile, as compared with the Comparative Example 2, the material of Example 1 has substantially improved surface roughness, and can substantially maintain the softness, smoothness, fitness of the base material to reduce the damage to surrounding tissues caused by friction, thereby reducing bleeding and inflammatory responses.

Embodiment 3

A surgical implant material for assisted repair of muscle mechanics was prepared by the same method of Example 1 except that:

1. The time of vortex shaking was 30 seconds;
2. The concentration of the aqueous solution of glutaraldehyde was 10%, and the time of immersion at 48° C. with magnetic stirring was 50 minutes;
3. The base material immersed in Step 3 was reacted at 60° C. in a vacuum environment of 0.5 Mpa for 10 min.

After detection, the above-prepared surgical implant material comprises 14.89% of nitrogen atom. After surface roughness detection, the material have a RMS surface roughness of 42.6 nm.

Embodiment 4

A surgical implant material for assisted repair of muscle mechanics was prepared by the same method of Example 1 except that:

1. a solution of collagen in hydrochloric acid was utilized;
2. the time of vortex shaking was 8 minutes;
3. the concentration of the aqueous solution of glutaraldehyde was 0.5%, and the time of immersion was 70 minutes;
4. the base material immersed in Step 3 was reacted at 120° C. in a vacuum environment of 0.2 Mpa for 15 min.

After detection, the above-prepared surgical implant material comprises 8.78% of nitrogen atom. After surface roughness detection, the material has a RMS surface roughness of 50.4 nm.

The invention claimed is:

1. A method of preparing a surgical implant material for assisted repair of gynecological pelvic floor muscles, comprising:

placing a net-like bacterial cellulose base material into a solution of collagen at a certain concentration, treating in a manner of vortex shaking for 30 seconds to 10 minutes, drying at room temperature;

placing the net-like bacterial cellulose base material into an aqueous solution of glutaraldehyde at a concentration of 0.5-10 wt % at 30-50° C., wherein the aqueous solution comprises a water-soluble inorganic aluminum salt, the aqueous solution is disturbed for immersion for 50-70 minutes; and immersing the net-like bacterial cellulose base material in a vacuum environment having a vacuum degree of 0.06-0.5 Mpa at 60-120° C. for 10-30 min, wherein the net-like bacterial cellulose base material undergoes a reaction to produce the surgical implant material for assisted repair of gynecological pelvic floor muscles, wherein the weight percentage of nitrogen atoms is 5-15% in the surgical implant material for assisted repair of gynecological pelvic floor muscles, and a surface of the material has a root-mean-square (RMS) roughness of 40-50 nm in the surgical implant material for assisted repair of gynecological pelvic floor muscles.

2. The method of preparing the surgical implant material for assisted repair of gynecological pelvic floor muscles of claim 1, wherein the water-soluble inorganic aluminum salt is present in the aqueous solution at a concentration of 0.1-3 wt %.

\* \* \* \* \*